United States Patent
Antanaitis

(10) Patent No.: US 8,562,522 B2
(45) Date of Patent: Oct. 22, 2013

(54) SURGICAL RETRACTOR

(76) Inventor: Girius Antanaitis, North Balwyn (AU)

(*) Notice: Subject to any disclaimer, the term of this patent is extended or adjusted under 35 U.S.C. 154(b) by 332 days.

(21) Appl. No.: 12/673,181

(22) PCT Filed: Jul. 15, 2008

(86) PCT No.: PCT/LT2008/000004
§ 371 (c)(1),
(2), (4) Date: Feb. 12, 2010

(87) PCT Pub. No.: WO2009/022887
PCT Pub. Date: Feb. 19, 2009

(65) Prior Publication Data
US 2011/0184246 A1    Jul. 28, 2011

(30) Foreign Application Priority Data
Aug. 10, 2007    (AU) ................... 2007904312

(51) Int. Cl.
*A61B 1/32* (2006.01)
(52) U.S. Cl.
USPC ........................................... 600/225; 600/226
(58) Field of Classification Search
USPC ................. 600/201, 210, 219, 222, 226
See application file for complete search history.

(56) References Cited

U.S. PATENT DOCUMENTS

| | | | | |
|---|---|---|---|---|
| 5,019,081 A * | 5/1991 | Watanabe | ................... | 606/79 |
| 5,303,694 A * | 4/1994 | Mikhail | ................... | 600/214 |
| 5,429,121 A * | 7/1995 | Gadelius | ................... | 600/217 |
| 5,967,972 A * | 10/1999 | Santilli et al. | ................... | 600/232 |
| 6,283,913 B1 * | 9/2001 | Seibel | ................... | 600/236 |
| 6,309,349 B1 * | 10/2001 | Bertolero et al. | ................... | 600/213 |
| 7,182,729 B2 * | 2/2007 | Abdelgany et al. | ................... | 600/219 |
| 7,722,613 B2 * | 5/2010 | Sutterlin et al. | ................... | 606/79 |
| 7,981,029 B2 * | 7/2011 | Branch et al. | ................... | 600/210 |
| 7,988,625 B2 * | 8/2011 | Abdelgany et al. | ................... | 600/220 |
| 2003/0055319 A1 * | 3/2003 | Chang | ................... | 600/210 |
| 2003/0153810 A1 | 8/2003 | Bertolero et al. | | |
| 2004/0225196 A1 | 11/2004 | Ruane | | |
| 2004/0254428 A1 * | 12/2004 | Ritland | ................... | 600/220 |
| 2005/0080320 A1 * | 4/2005 | Lee et al. | ................... | 600/214 |
| 2005/0177173 A1 * | 8/2005 | Aebi et al. | ................... | 606/105 |
| 2005/0267336 A1 * | 12/2005 | Bertolero et al. | ................... | 600/219 |
| 2007/0027364 A1 | 2/2007 | Schwer | | |
| 2007/0123753 A1 * | 5/2007 | Abdelgany et al. | ................... | 600/220 |

FOREIGN PATENT DOCUMENTS

| | | |
|---|---|---|
| WO | 03/017847 | 3/2003 |
| WO | 2007/068128 | 6/2007 |

OTHER PUBLICATIONS

International Search Report dated Apr. 1, 2009, from corresponding PCT application.

* cited by examiner

*Primary Examiner* — Ellen C Hammond
(74) *Attorney, Agent, or Firm* — Young & Thompson

(57) ABSTRACT

A surgical retractor including a pair of handles mounted for pivotal movement about a pivot pin, a pair of arm members each terminating at a distal end in a downwardly depending blade and attachable to a respective handle at a proximal end. On application of hand pressure by an operator to the pair of handles of the surgical retractor rotates each handle and arm member about the pivot pin and causes the blades to move apart so that in use in a surgical site the blades abut against and retract tissue matter.

20 Claims, 4 Drawing Sheets

SURGICAL RETRACTOR

FIELD OF THE INVENTION

This invention relates to a surgical retractor for use in surgical procedures.

BACKGROUND OF THE INVENTION

In order to obtain optimal exposure to a surgical site, after a surgeon has made an incision to a body, it is often necessary to use at least one retractor to expose the underlying layers of tissue.

Some existing surgical retractors include single bladed retractors, such as the Langenbeck retractor. The single bladed retractors are used to retract one side of a surgical incision in order to hold tissues clear of a surgical site. Such single bladed retractors must be continually held by an assistant or the surgeon and often multiple retractors are needed to retract skin, ligaments and muscle tissue around the incision, requiring both hands of the surgical assistant. Often these retractors are not self-retaining and thus continuous holding of the retractors by assistants is required. In such situations, the forces required to be exerted on the retractors can induce fatigue on the operators, particularly in lengthy operations, or for example, when operating on muscle-bound or even obese patients.

Thus, during a surgical procedure, a surgeon or the assistant will use one or more such single bladed retractors to expose the area that is to be operated on. The surgical assistant uses the retractor to keep the exposed area open. More than one single bladed retractor can be used in operations where more retraction is desirable for optimal surgical exposure.

Other handheld-type retractors include those that work on a scissor action in that the fingers of the operator are gripped through ring-shaped handles in order to move blades attached to levers inwardly and outwardly about a pivot point. Generally, they include a self-retaining mechanism in order to keep the blades apart at a set distance within the wound or surgical site. Specific problems with scissor action retractors are that an excessive amount of force may have to be applied in order to retract the levers and therefore the blades at the surgical site, and that the maximum extension or retraction may still not provide enough access for a surgeon to operate within.

Other retractors include multiple blades that can be separate from the retractor body or are attached to the retractor body by sliding arms. These retractors are typically locked into place by a butterfly nut, and for those that have separate blades, use the tension of human tissue to retain its place on the body of the retractor. Some of these self-retaining retractors are attached to a frame which is then attached to the surgical table or bed. These types of retractors are bulky, expensive and can be difficult and time consuming to set up.

Document WO03/017847 discloses an axillary clearance surgical device which has a pair of pivoting arms movable relative to each other and adapted to hold apart sides of a surgical incision. It also includes a substantially L-shaped retractor which is releasably mounted to a retaining element 14. The device is generally mounted to a support arm which is secured to an operating table during a surgical procedure. This is done to maintain the device in a desired position. The retractor disclosed in this document does not provide for hand-held use but instead requires connection through a support arm to the operating table for specific axillary clearance surgery.

In U.S. patent application No. 2004/225196 there is disclosed a surgical retractor consisting of a complex series of components in which the angular position of a pair of blades is adjustable by means of a pair of wires that extend from the blades to an adjustment screw located near the handles. There is no disclosure in this document of a pair of handles that can be rotated towards each other to thereby separate arm members and blades located at respective ends of the arm members when used in a surgical procedure to retract and hold apart tissue, without the use of adjustment wires.

In document WO2007/068128 there is disclosed a pair of tongs including a pair of handles and blades and a locking mechanism that includes a release member which allows the locking mechanism to be disengaged from a desired retracted position. Applying pressure to the handles separates the blades in a scissor-like manner in order to attract tissue. Furthermore, the handles are resiliently spread apart when the locking mechanism is disengaged.

In U.S. Pat. No. 6,283,913 there is disclosed a lid speculum that is used to retract an eyelid of an eye and has a pair of blades that are arranged to move in a radial direction corresponding to the shape of the eyeball. The device is suited only for eyelid retraction and is not applicable to retract tissue at a surgical site.

The present invention seeks to overcome one or more of the above disadvantages by providing a surgical retractor that can be held in one hand by the operator and can be used for an extended period of time during a surgical procedure. The surgical retractor of the present invention is made easier to use by an operator in that it uses a pivoting action when handles of the retractor are forced towards one another in order to spread apart respective blades of the surgical retractor. The present invention can allow a surgical assistant to retain a free hand for other tasks, such as retracting, cutting or clamping. It also provides the potential to allow for a relatively small incision by enabling better access to deeper tissues around the apices of the incision.

SUMMARY OF THE INVENTION

The invention provides a surgical retractor comprising:

a pair of handles mounted for pivotal movement about a pivot pin having a pivot axis;

a pair of arm members each terminating at a distal end in a downwardly depending blade and attachable to a respective handle at a proximal end, each arm member in a non-use state being in a position substantially parallel to the pivot axis and to each other;

characterised in that application of pressure to the pair of handles causes each handle and arm member to rotate about the pivot axis such that each handle rotates towards the other handle which causes the arm members to move apart in different planes so that in use in a surgical site the blades abut against and retract tissue matter.

Preferably on release of hand pressure applied to the handles, the arm members return to a position such that the arm members are adjacent and substantially parallel to one another.

Each handle may be offset from a pivot axis of the pivot pin to provide a moment about the pivot axis when pressure is applied to each handle so that each handle can rotate about the pivot axis and pivot pin.

Each arm member may have a downwardly curved section near the proximal end of the respective arm member so as to create an offset A between each arm member and the pivot axis of the pivot pin. The offset A enables the arm members and therefore the blades to have a greater maximum separation distance than would otherwise be available without such an offset.

A distance B between each arm member may be formed when the arm members are substantially perpendicular to one another. For each blade that depends directly downwardly from a respective arm member, the blades are substantially perpendicular to one another when the arm members are substantially perpendicular to each other. Preferably when distance B equals offset A, the retractor is in a fully retracted and open position when the arm members are substantially perpendicular to one another. Preferably offset A is the distance from the top surface of each arm member and the pivot axis of the pivot pin. An operator is able to select a set of arm members and blades for a surgical task by knowing offset A and distance B.

At a distal end of each of the handles there is a first or rear flange to assist the user in gripping the handles. At a proximal end of each of the handles there is preferably a second or front flange. The front flange of either or both handles may be used to mount a locking means. The locking means may be finger-operated by the user so as to engage and disengage the retractor in and from a fixed position in which the arm members and blades are apart by a fixed distance. Preferably the locking means is a ratchet locking mechanism in which a transverse member has a series of teeth adapted to engage a corresponding tooth or teeth located on one of the handles.

Preferably the pivot pin is located to engage bosses each forming part of the handles so that the pivot pin is located through each of the bosses to link each handle. A resilient means, preferably in the form of a spring, is used to enable the retractor to return to its original state, in which the arm members are parallel to one another. This can be done by release of the locking means or release of hand pressure on the handles.

Each arm member may be attached to a respective handle through fastening means, such as screws or rivets. Most preferably the arm members are interchangeable in that each pair of arm members can be locked or made to snap fit with each handle so that the arm members can be easily attached and detached from the respective handle.

The blades may depend downwardly at substantially right angles to the longitudinal axis of each arm member or at another angle, for example at 45 degrees to the longitudinal axis of each arm member. At the distal end of each blade there is preferably a foot, curved inwardly, to assist in retracting any tissue at the surgical site.

Each arm member and depending blade may be considered as a single blade in specific surgical procedures such as endoscopic, keyhole or laparoscopic surgery.

BRIEF DESCRIPTION OF THE DRAWINGS

Preferred embodiments of the invention will hereinafter be described, by way of example only, with reference to the drawings wherein.

DETAILED DESCRIPTION OF THE PREFERRED EMBODIMENTS

Figure 1:
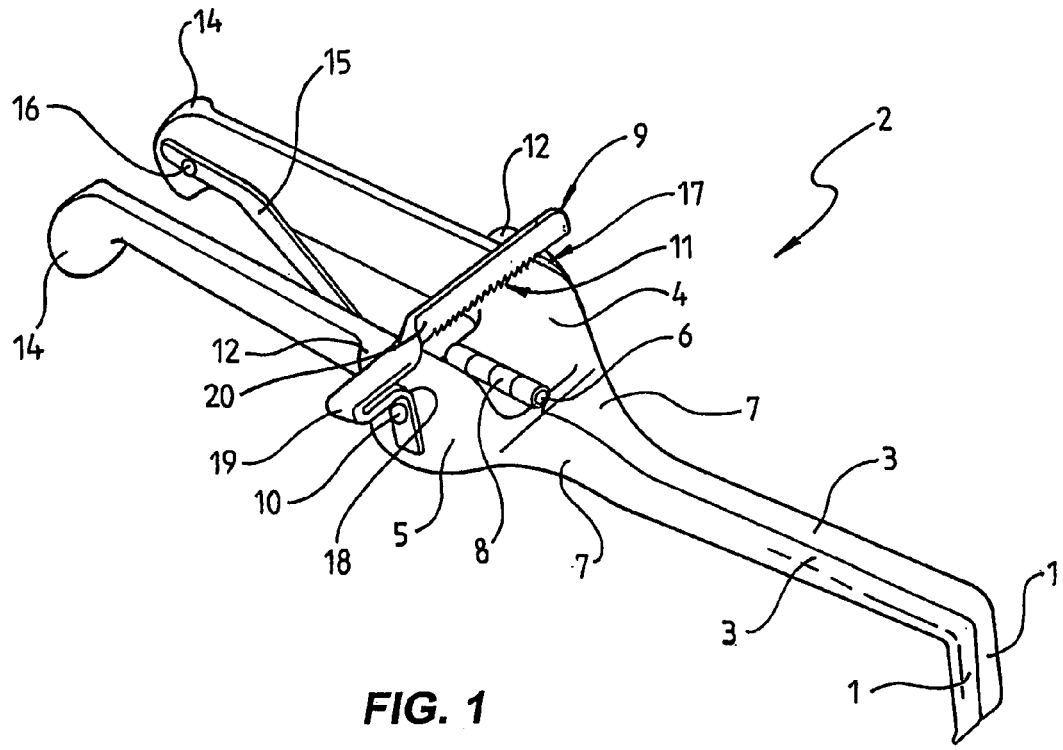
FIG. 1 is a perspective view from above of a surgical retractor in accordance with an embodiment of the invention.

With reference to FIG. 1 there is shown a surgical retractor 2 having a pair of handles 4,5 and a pair of arm members 3. Downwardly depending from a distal end of each of the arm members 3 is a blade 1. Each of the blades 1 are shown as depending perpendicularly from a longitudinal axis of the arm members 3 but can be arranged at an angle to the longitudinal axis of each member 3, such as 45°. At the lower end of each blade 1 is a foot 13 that is curved inwardly from the plane of the blade. The blades 1, together with the feet 13, assist in abutting against and retracting tissue at a surgical site. Each of the arm members 3 are fastened to respective handles 4 and 5 at a proximal end of the arm members 3. Suitable fastening means can include screws, rivets or snap-fit connectors.

The handles 4 and 5 are connected to one another through a pivot mechanism 8 made up of a pivot pin 6 and respective bosses that are attached to each handle 4 and 5 and through which the pivot pin 6 protrudes. The pivot pin 6 can be kept in place by a securing means.

Figure 2:
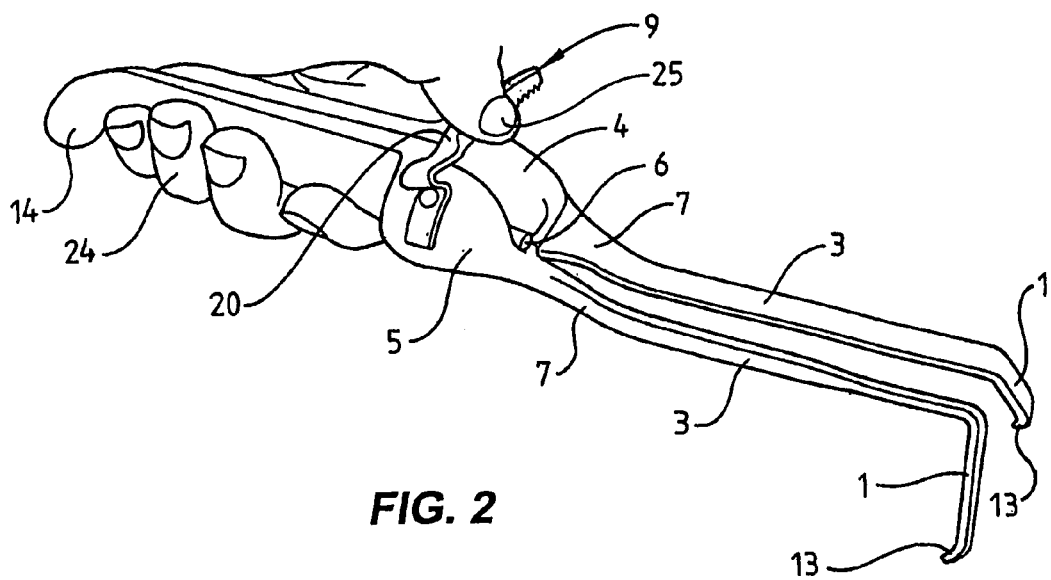
FIG. 2 is a perspective view of the surgical retractor of FIG. 1 showing arm members of the retractor in a fully open position and wherein the operator is about to release a position locking mechanism in order to enable the arm members to move towards each other.

Mounted to a front flange 12 of one of the handles 5 is a locking mechanism 9 that is able to hold the retractor 2 and more particularly the blades 1 and arm members 3 at a predefined distance apart when used in a surgical site. The locking mechanism 9 is operated by the thumb 25 of the operator, as seen in FIG. 2, whereby a lateral flexible section 20 is able to be manipulated by the operator to engage and disengage a series of teeth 11 on the lower side of the flexible section 20 with one or more teeth 17 that are located on an upper section of front flange 12 of handle 4. Thus, the teeth 17 and 11 engage at a required separation distance of the arm members as required by the user. The locking mechanism acts as a ratchet, and in particular a saw tooth ratchet, by the engagement and disengagement of the teeth. The locking mechanism 9 is attached to the front flange 12 of handle 5 through a suitable fastener 10. Above the lower protruding section that is fastened to the front flange 12 are two horizontal flexible sections 18 and 19 that are doubled against each other so that they create a curve and are parallel to each other. The flexible section 20 is an extension of the horizontal flat section 19.

A resilient mechanism in the form of spring 15 is attached to a rear flange 14 of handle 4 through a fastener 16. The spring 15 is a flat spring and is attached at its other end to the pivoting mechanism 8. The spring 15 enables the retractor 2 to return to its original closed position as seen in FIG. 1.

The front flange 12 improves the controllability of the retractor 2 if pushing or otherwise vigorous manipulation of the retractor 2 is necessary during a procedure. The rear flange 14 assists the operator to keep a firm grip when retracting in a pulling motion. It also reduces slip and increases the amount of force that can be transferred from the hand to the point of retraction. It also reduces fatigue on the operator's hand.

Referring to FIG. 2 it is seen that a user, by applying pressure to each of the handles 4 and 5 through fingers of one hand, imparts a rotational force on each of the handles 4 and 5 so that they pivot about the pivot pin 6 towards each other. This action in turn separates the arm members 3 and also the blades 1 as see in FIG. 2. The user's forefinger abuts against one of the front flanges 12 whilst the little finger of the same hand is adjacent the rear flange 14. The user is able to lock the locking mechanism 9 through the respective teeth 11 and 17 at a required separation distance of the arm members 3 and blades 1. This is simply done by lifting the locking mechanism teeth 11 over corresponding teeth 17 whilst applying force to the handles 4 and 5. Release of the ratchet locking mechanism 9 is performed by deflecting flexible member 20 to release teeth 11 from teeth 17 so that the retractor 2 can return to its original position. The action of the spring 15 also maintains the surgical retractor 2 in a locked position and it is the force provided by the spring 15 against which the user's hands operate in order to retract the arm members 3 and blades 1.

At the proximal end of each of the arm members 3 there is a curved section 7 between where the arm member 3 attaches to a respective handle such that curved section 7 of each arm member 3 depends downwardly so that there is an offset or a small distance between the plane of the top of each of the arm members 3 and the pivot axis of the pivot pin 6. This offset assists in providing a greater gap between the blades 1 at the surgical site.

Figure 3:
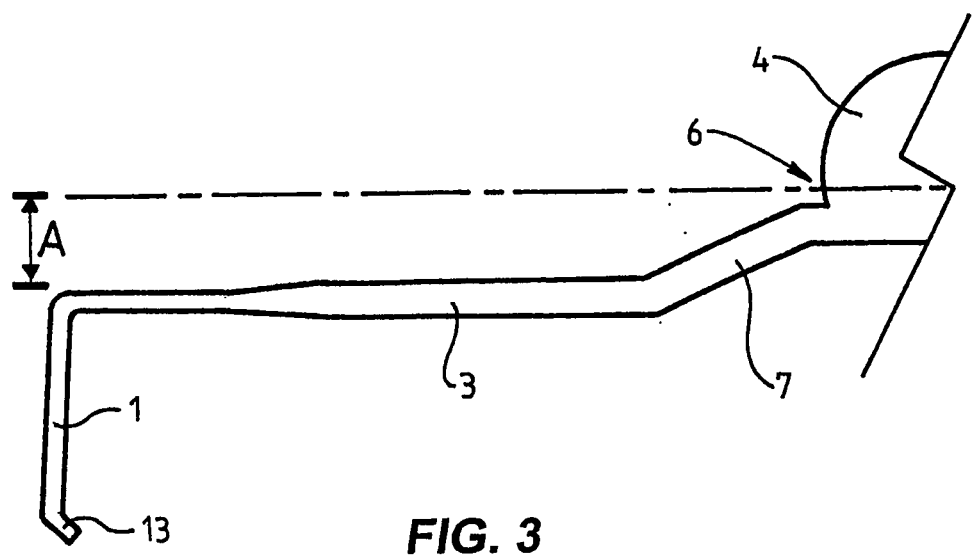
FIG. 3 is a side view of the arm members and blades of the surgical retractor.

With reference to FIG. 3, it is seen that the offset A represents the distance between the pivot axis of pivot pin 6 and the top of each arm member 3.

Figure 4:
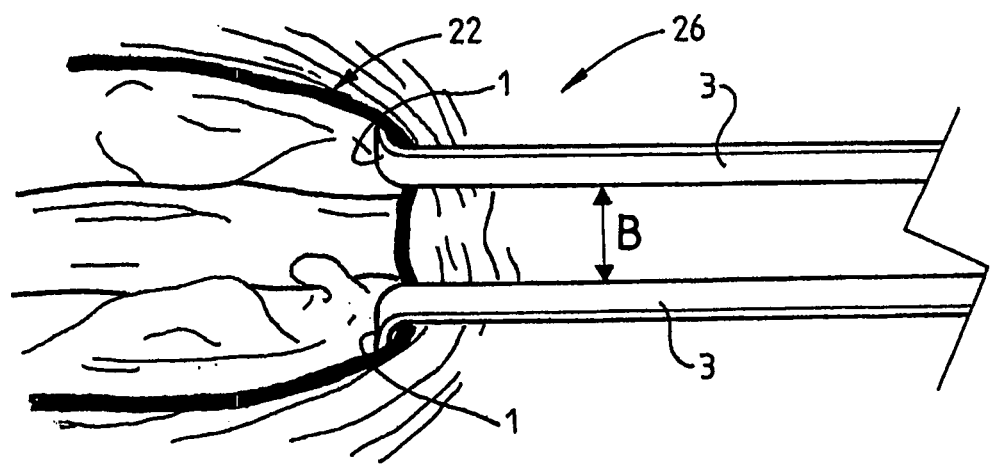
FIG. 4 is a view from above of the surgical retractor of FIG. 1 in use at a surgical site whereby the blades abut against and retract tissue at the surgical site in a fully open position.

Referring to FIG. 4 there is shown the blades 1 abutting against and retracting tissue 22 with a separation distance B between the inner sides of the top faces of each of the arm members 3. Distance B will equal distance A in a fully open position 26, shown in FIG. 4, when each of the blades are substantially at 90° to one another. This is the case for blades 1 that substantially depend directly downwardly from the arm members 3 so that when the blades are at 90° to one another then so too the arm members 3 will be at 90° to one another. In situations where the blades 1 are at 45° to the longitudinal axis of each of the arm members 3 then the separation distance at the wound site will be even greater. By knowing the distance A and B, the surgeon or operator can select the most suitable sized set of arm members and blades for the particular surgical task. The blades, in particular, are available in various sizes and shapes, and can be selected as needed.

Figure 5:
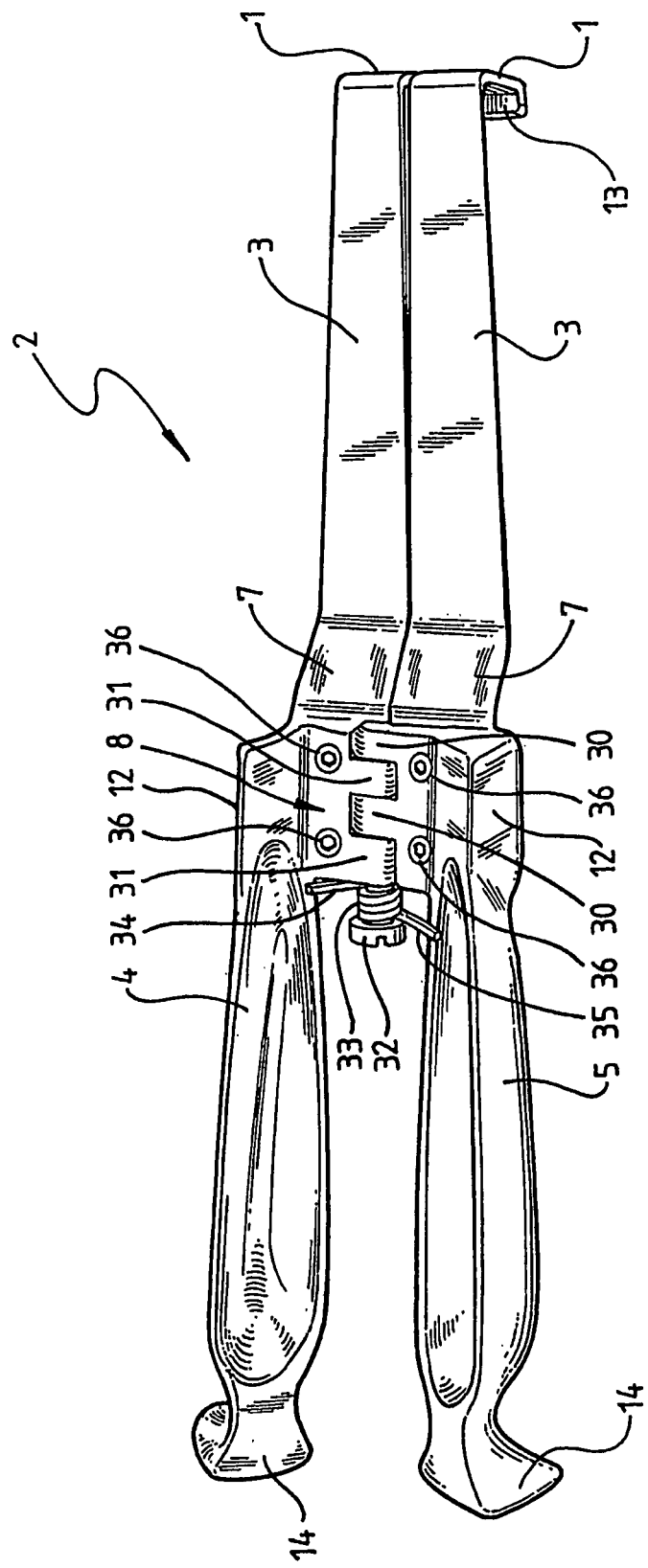
FIG. 5 is a view from above of a surgical retractor according to a further embodiment.
Figure 6:
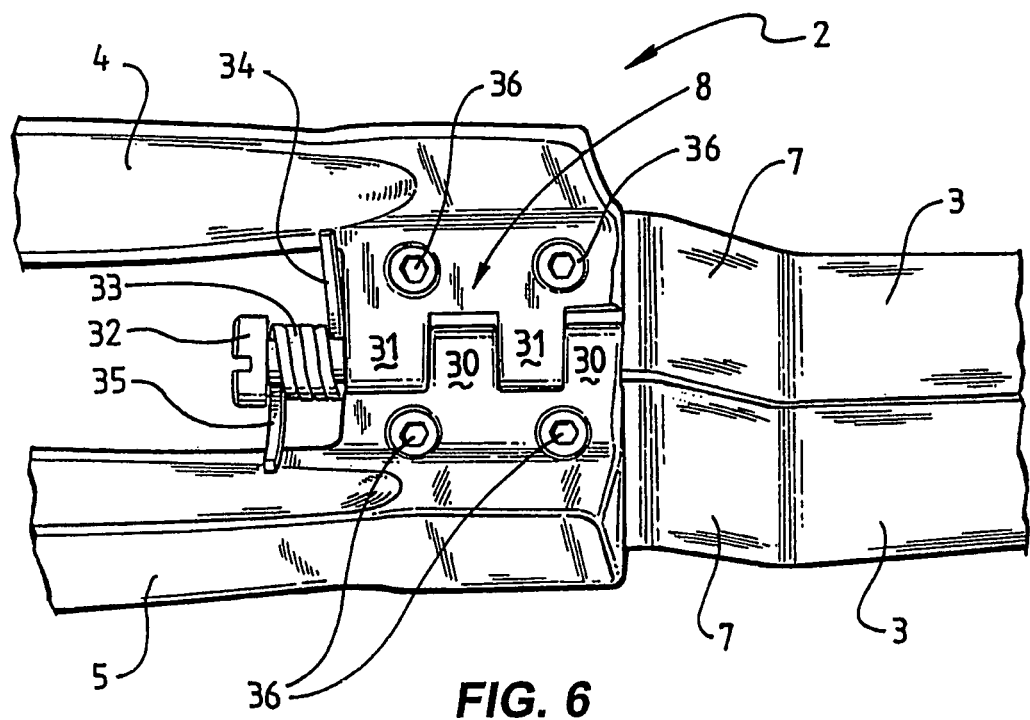
FIG. 6 is a view from above of the surgical retractor of FIG. 5 showing in more detail the connection of the arm members to the handles and the pivot mechanism.

Referring to FIGS. 5 and 6 there is shown a further embodiment of the surgical retractor 2. This retractor is shown without any locking mechanism and has a pivoting mechanism 8 that includes a resilient member 33 acting in co-operation with a pivot pin (not shown). Surrounding the pivot pin are a pair of bosses 31 that protrude from an inner section of handle 4 and similarly a pair of bosses 30 separated one from the other and interlocking with the respective bosses 31, the bosses 30 protruding from an inner section of handle 5. Each of the bosses 30 and 31 have the pivot pin protruding therethrough and located between each of the handle sections 4 and 5 is the head of a bolt 32 which is contiguous with pivot pin 6. Housed between the head of the bolt 32 and one of the bosses 31 is resilient means in the form of a spring 33 that has one end 35 abutting the inner section of handle 5 and a second end 34 abutting the inner section of handle 4. The requisite tension on the spring can be adjusted through the bolt head 32. Each of the arm members 3 are attached via respective fastening means 36 to respective handle 4 and 5. The particular fastening means shown is screws having an Allen key head but any other suitable fastening means may be used.

Thus, in use the surgeon or other operator of the surgical retractor 2 would grip each of the handles 4 and 5 in the gripping sections intermediate flanges 12 and 14 and apply pressure to the handles 4,5 inwardly so that they rotate about the pivot pin 6 and the user produces a force against the force of the spring 33. The handles 4 and 5 rotate about the pivot pin 6 which in turn forces the arm members 3, and therefore the blades 1, to separate outwardly. A locking mechanism may be attached to the surgical retractor 2 in FIGS. 5 and 6 in order to lock the retractor in a desired position with the arm members 3 and blades 1 a set distance apart.

Figure 7:
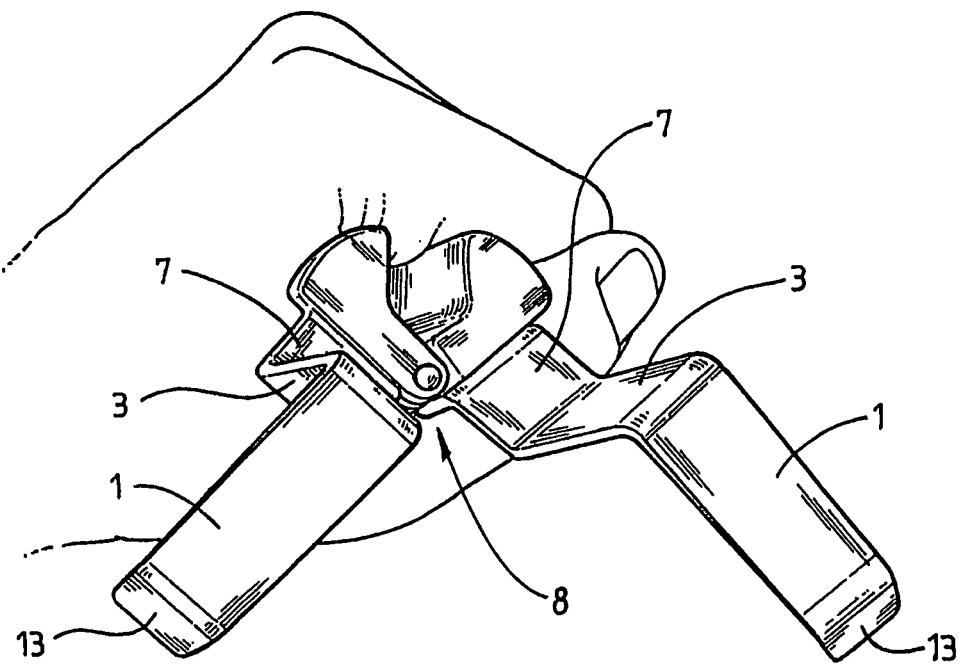
FIG. 7 is a view showing the surgical retractor in a fully open position.

Shown in FIG. 7 is the surgical retractor shown in a fully open position with the blades 1 substantially forming a right angle between their respective axes. As can be seen, the resulting grip of the operator shows each of the handle sections 4 and 5 rotated about the pivot pin 6. Arm members 3 also have their top faces substantially perpendicular to one another.

The surgical retractor 2 of the present invention can be used for general surgery and orthopaedic surgery. The retractor 2 can be downsized for microsurgery and minimally invasive surgery. The retractor 2 can be gripped in either hand. It can retract flesh at the apex of the incision or anywhere laterally along the wound or incision. When used at the apex of an incision, the retractor 2 will minimise tissue damage at the surface, since the widest opening of the blades is inside the wound. Fatigue and tearing will therefore be reduced at the apex as a smaller incision can be used.

Stainless steel is the preferred material from which the retractor 2 is made but it is possible to use titanium alloys and polymers. The retractor 2 can perform the task of two single-bladed retractors, thus leaving a free hand of the operator to perform other duties. This can reduce the number of assistants needed during an operation and therefore make available more room in the operating theatre and also save time.

Each arm member 3 and depending blade 1 may be considered as a single blade in specific surgical procedures such as endoscopic, keyhole or laparoscopic surgery. The complete retractor (including arm members and blades) or just the arm members and blades can be used once only and then disposed of in particular operating circumstances, for example, in environments where it is not possible, or too difficult, to sterilise the retractor and/or its parts. Thus the retractor 2 can be manufactured for single use (disposable) or to be reusable for many operations.

What is claimed is:

1. A surgical retractor (2) comprising:
   first and second handles (4,5) mounted for pivotal movement about a pivot pin (6) having a pivot axis, the first and second handles (4,5) being constructed and arranged to simultaneously be held by a single hand of a user, the first and second handles (4,5) extending along a first longitudinal axis;
   first and second arm members (3) each terminating at a distal end in a downwardly depending blade (1) and attachable respectively to the first and second handles (4,5) at a proximal end, the first and second arm members (3) extending along a second longitudinal axis parallel to the first longitudinal axis, each arm member (3) in a closed position being in a position substantially parallel to the pivot axis and to each other;
   wherein application of pressure to the first and second handles (4,5) by the single hand of the user causes each handle (4,5) and arm member (3) to rotate about the pivot axis such that each handle (4,5) rotates towards the other handle (5,4) which causes the arm members (3) to move apart in different planes so that in use in a surgical site the blades (1) abut against and retract tissue matter (22).

2. A surgical retractor (2) according to claim 1 further comprising a resilient means (15,33) to enable the arm members (3) to return to the position in the closed position such that the arm members (3) are adjacent and substantially parallel to one another upon release of the pressure applied to the handles (4,5).

3. A surgical retractor (2) according to claim 2 wherein each handle (4,5) is offset from the pivot axis of the pivot pin (6) to provide a moment about the pivot axis when pressure is applied to each handle (4,5) so that each handle (4,5) rotates about the pivot axis and pivot pin (6).

4. A surgical retractor (2) according to claim 2 wherein each arm member (3) has a downwardly curved section (7) near the proximal end of the respective arm member (3) so as to create an offset A between a top surface of each arm member (3) and the pivot axis of the pivot pin (6).

5. A surgical retractor (2) according to claim 1 wherein each handle (4,5) is offset from the pivot axis of the pivot pin (6) to provide a moment about the pivot axis when pressure is applied to each handle (4,5) so that each handle (4,5) rotates about the pivot axis and pivot pin (6).

6. A surgical retractor (2) according to claim 5 wherein each arm member (3) has a downwardly curved section (7) near the proximal end of the respective arm member (3) so as to create an offset A between a top surface of each arm member (3) and the pivot axis of the pivot pin (6).

7. A surgical retractor (2) according to claim 1 wherein each arm member (3) has a downwardly curved section (7) near the proximal end of the respective arm member (3) so as to create an offset A between a top surface of each arm member (3) and the pivot axis of the pivot pin (6).

8. A surgical retractor (2) according to claim 7 wherein for each blade (1) that depends directly downwardly from a respective arm member (3), the blades (1) are substantially perpendicular to one another when the arm members (3) are substantially perpendicular to each other.

9. A surgical retractor (2) according to claim 8 wherein a distance B between each arm member (3) equals offset A, when the retractor (2) is in a fully retracted and open position and the arm members (3) are substantially perpendicular to one another.

10. A surgical retractor (2) according to claim 1:
wherein the first arm member (3) extends directly from the first handle (4) monolithically;
wherein the second arm member (3) extends directly from the second handle (5) monolithically.

11. A surgical retractor (2) comprising:
first and second handles (4,5) mounted for pivotal movement about a pivot pin (6) having a pivot axis;
first and second arm members (3) each terminating at a distal end in a downwardly depending blade (1) and attachable respectively to the first and second handles (4,5) at a proximal end, each arm member (3) in a closed position being in a position substantially parallel to the pivot axis and to each other;
wherein application of pressure to the first and second handles (4,5) causes each handle (4,5) and arm member (3) to rotate about the pivot axis such that each handle (4,5) rotates towards the other handle (5,4) which causes the arm members (3) to move apart in different planes so that in use in a surgical site the blades (1) abut against and retract tissue matter (22)
wherein further comprising:
a front flange (12) at one end and a rear flange (14) at a second end of each of the handles (4,5) to assist the operator in gripping the handles (4,5); and
a locking means (9) mounted on the front flange (12) of both handles (4,5).

12. A surgical retractor (2) according to claim 11 wherein the locking means (9) is finger-operatable so as to engage and disengage the retractor (2) in and from a fixed position in which the arm members (3) and blades (1) are apart by a fixed distance.

13. A surgical retractor (2) according to claim 12 wherein the locking means (9) is a ratchet locking mechanism in which a transverse member (20) has a series of teeth (11) adapted to engage a corresponding tooth or teeth (17) located on one of the handles (4,5).

14. A surgical retractor (2) according to claim 13 wherein each handle (4,5) has one or more interlocking bosses (30,31) such that the pivot pin (6) is located through and engages with each of the one or more bosses (30,31) so as to link each handle (4,5).

15. A surgical retractor (2) according to claim 12 wherein each handle (4,5) has one or more interlocking bosses (30,31) such that the pivot pin (6) is located through and engages with each of the one or more bosses (30,31) so as to link each handle (4,5).

16. A surgical retractor (2) according to claim 11 wherein each handle (4,5) has one or more interlocking bosses (30,31) such that the pivot pin (6) is located through and engages with each of the one or more bosses (30,31) so as to link each handle (4,5).

17. A surgical retractor (2) comprising:
first and second handles (4,5) connected through a pivot pin (6) having a pivot axis, the first and second handles (4,5) being constructed and arranged to simultaneously be held by a single hand of a user, the first and second handles (4,5) extending along a first longitudinal axis;
first and second arm members (3) each terminating at a distal end in a downwardly depending blade (1) and attachable respectively to the first and second handles (4,5) at a proximal end, the first and second arm members (3) extending along a second longitudinal axis parallel to the first longitudinal axis, each arm member (3) in a closed position being in a position substantially parallel to the pivot axis and to each other;
wherein application of pressure to the first and second handles (4,5) by the single hand of the user causes each handle (4,5) and arm member (3) to rotate about the pivot axis such that each handle (4,5) rotates towards the other handle (5,4) which causes the arm members (3) to move apart in different planes so that in use in a surgical site the blades (1) abut against and retract tissue matter (22).

18. A surgical retractor (2) according to claim 17 further comprising a resilient means (15,33) to enable the arm members (3) to return to the position in the closed position such that the arm members (3) are adjacent and substantially parallel to one another upon release of the pressure applied to the handles (4,5).

19. A surgical retractor (2) according to claim 17 wherein each handle (4,5) is offset from the pivot axis of the pivot pin (6) to provide a moment about the pivot axis when pressure is applied to each handle (4,5) so that each handle (4,5) rotates about the pivot axis and pivot pin (6).

20. A surgical retractor (2) according to claim 17:
wherein the first arm member (3) extends directly from the first handle (4) monolithically;
wherein the second arm member (3) extends directly from the second handle (5) monolithically.

* * * * *